United States Patent
Esco et al.

(10) Patent No.: US 12,179,060 B2
(45) Date of Patent: *Dec. 31, 2024

(54) AUTOMATED AEROBIC FITNESS MEASUREMENT FROM SMARTPHONE TECHNOLOGY

(71) Applicant: The Board of Trustees of The University of Alabama, Tuscaloosa, AL (US)

(72) Inventors: Michael R. Esco, Northport, AL (US); Michael V. Fedewa, Northport, AL (US)

(73) Assignee: The Board of Trustees of The University of Alabama, Tuscaloosa, AL (US)

(*) Notice: Subject to any disclaimer, the term of this patent is extended or adjusted under 35 U.S.C. 154(b) by 220 days.

This patent is subject to a terminal disclaimer.

(21) Appl. No.: 17/692,501

(22) Filed: Mar. 11, 2022

(65) Prior Publication Data

US 2022/0331660 A1 Oct. 20, 2022

Related U.S. Application Data

(60) Provisional application No. 63/159,583, filed on Mar. 11, 2021.

(51) Int. Cl.
*A63B 24/00* (2006.01)
*A61B 5/00* (2006.01)
(Continued)

(52) U.S. Cl.
CPC ........ *A63B 24/0062* (2013.01); *A61B 5/4872* (2013.01); *G06T 7/62* (2017.01);
(Continued)

(58) Field of Classification Search
CPC .......... A61B 5/4872; A63B 2024/0065; A63B 2220/17; A63B 2220/807; A63B 2230/01;
(Continued)

(56) References Cited

U.S. PATENT DOCUMENTS 9,237,868 B2 1/2016 Seppanen et al.
9,526,442 B2 12/2016 Moore et al.
(Continued)

FOREIGN PATENT DOCUMENTS

JP 6196024 B2 9/2017
KR 20130134680 A * 12/2013 ............. G06T 17/00
(Continued)

OTHER PUBLICATIONS

Translated Park 20130134680 (Year: 2013).*
(Continued)

*Primary Examiner* — Katherine L Fernandez
*Assistant Examiner* — Brooke Lyn Klein
(74) *Attorney, Agent, or Firm* — Meunier Carlin & Curfman LLC

(57) ABSTRACT

Methods and systems are provided for measuring anatomical dimensions from a single two-dimensional (2D) digital image. The digital image is taken from the front/anterior view using a mobile, handheld communication device. The linear measurements are used to estimate the body volume of the individual. Total body density is calculated from estimated body volume and body weight. Body composition (fat mass and fat-free mass) of the individual is derived from density using known mathematical conversion formulas. A method for estimating body composition analysis is provided. Systems and methods are provided that determine an individual's fitness by determining body composition of the individual using a picture of the individual, determining the individual's VO$_2$ max based on the individual's movement
(Continued)

(e.g., walking and/or running a measured distance over a measured amount of time), and determining the individual's fitness based on the body composition and the determined $VO_2$ max.

11 Claims, 8 Drawing Sheets

(51) Int. Cl.
*G06T 7/62* (2017.01)
*G06T 7/73* (2017.01)
*G06V 40/10* (2022.01)

(52) U.S. Cl.
CPC .............. *G06T 7/73* (2017.01); *G06V 40/103* (2022.01); *A63B 2024/0065* (2013.01); *A63B 2220/17* (2013.01); *A63B 2220/807* (2013.01); *A63B 2230/01* (2013.01); *A63B 2230/06* (2013.01); *A63B 2230/70* (2013.01); *G06T 2207/30196* (2013.01)

(58) Field of Classification Search
CPC ............ A63B 2230/06; A63B 2230/70; A63B 24/0062; G06T 2207/10004; G06T 2207/30196; G06T 7/0012; G06T 7/62; G06T 7/73; G06V 10/25; G06V 20/64; G06V 40/103

See application file for complete search history.

(56) References Cited

U.S. PATENT DOCUMENTS

| | | | |
|---|---|---|---|
| 9,788,759 B2 | 10/2017 | Ferrantelli et al. | |
| 9,801,550 B2 | 10/2017 | Ferrantelli et al. | |
| 10,019,721 B2 | 7/2018 | Ackland et al. | |
| 10,413,250 B2 | 9/2019 | LeBeouf et al. | |
| 2010/0245555 A1 | 9/2010 | Talluri et al. | |
| 2010/0292598 A1 | 11/2010 | Roschk et al. | |
| 2012/0232360 A1* | 9/2012 | Maueler | A61B 5/6892 600/301 |
| 2013/0261470 A1 | 10/2013 | Allison et al. | |
| 2014/0025346 A1 | 1/2014 | Uchiyama | |
| 2014/0031700 A1 | 1/2014 | Ferrantelli et al. | |
| 2015/0223730 A1 | 8/2015 | Ferrantelli et al. | |
| 2016/0088284 A1 | 3/2016 | Sareen et al. | |
| 2016/0247017 A1 | 8/2016 | Sareen et al. | |
| 2017/0353711 A1 | 12/2017 | Wayenberg | |
| 2019/0347817 A1* | 11/2019 | Ferrantelli | G06F 18/217 |
| 2020/0345314 A1 | 11/2020 | Fedewa et al. | |
| 2021/0287804 A1 | 9/2021 | Barnes | |
| 2021/0358633 A1 | 11/2021 | Barnes | |
| 2022/0087533 A1 | 3/2022 | El-Sallam et al. | |
| 2022/0304619 A1 | 9/2022 | Merchant et al. | |

FOREIGN PATENT DOCUMENTS

| | | |
|---|---|---|
| KR | 1020180038251 | 4/2018 |
| WO | 2017/008118 | 1/2017 |
| WO | 2017/168805 | 10/2017 |
| WO | 2020/132713 | 7/2020 |

OTHER PUBLICATIONS

Borga, Magnus, et al. "Advanced body composition assessment: from body mass index to body composition profiling." Journal of Investigative Medicine 66.5 (2018): 1-9.
Affuso, Olivia, et al. "A method for measuring human body composition using digital images." PloS one 13.11 (2018): e0206430.
Shaw, Matthew P., Joshua Robinson, and Daniel J. Peart. "Comparison of a mobile application to estimate percentage body fat to other non-laboratory-based measurements." Biomedical Human Kinetics 9.1 (2017): 94-98.
Wells, Jonathan CK. "Sexual dimorphism of body composition." Best practice & research Clinical endocrinology & metabolism 21.3 (2007): 415-430.
Steven B. Heymsfield and ZiMian Wang Richard N. Baumgartner Robert Ross, "Human Body Composition: Advances in Models and Methods." Annual Review of Nutrition 1997 17:1, 527-558 (1997), pp. 527-558.
Body Composition Technologies; web-page; Sep. 1, 2018; retrieved Sep. 30, 2021 from Internet Archive Wayback Machine.
Notice of Allowance issued for U.S. Appl. No. 16/841,944, dated Jun. 7, 2023.
Office Action issued for U.S. Appl. No. 16/841,944, dated Mar. 2, 2023.
Office Action issued for U.S. Appl. No. 16/841,944, dated Aug. 18, 2022.
Dan E. Webster, et al., Heart Snapshot: a broadly validated smartphone measure of VO 2 max for collection of real world data. bioRxiv preprint doi: https://doi.org/10.1101/2020.07.02.185314; posted Jul. 4, 2020. https://www.biorxiv.org/content/10.1101/2020.07.02.185314v1.full).
Clnet, Vanessa Hand Orellana , Anew Apple Watch alert tells you how fit (or unfit) you are. Here's how to get it. Dec. 17, 2020 https://www.cnet.com/news/new-apple-watch-alert-tells-you-how-fit-or-unfit-you-are-cardio-fitness-score-vo2-max-notification/.

\* cited by examiner

AUTOMATED AEROBIC FITNESS MEASUREMENT FROM SMARTPHONE TECHNOLOGY

CROSS-REFERENCE TO RELATED APPLICATIONS

This application claims benefit of U.S. Provisional Patent Application No. 63/159,583, filed on Mar. 11, 2021, entitled "AUTOMATED AEROBIC FITNESS MEASUREMENT FROM SMARTPHONE TECHNOLOGY," the contents of which are hereby incorporated by reference in their entirety.

BACKGROUND

Measurement of body composition (fat mass and fat-free mass) can be obtained using highly accurate techniques such as dual energy x-ray absorptiometry (DXA), air displacement plethysmography (ADP), or underwater weighing (UWW). However, these methods are not widely used in field settings due, in part, to their inability to be transported, as well as the cost and size of the equipment used. In addition, many of these methods cannot accommodate the dimensions of taller and heavier individuals that may exceed the scanning area, are too large for the measurement chamber, or cannot completely submerge underwater. Furthermore, individuals who may become claustrophobic or are unable to safely access the equipment because of mobility limitations may also experience difficulties when using the previously mentioned techniques. Moreover, DXA is often used in clinical settings, but exposes the technician and participants to radiation, which may limit the use of DXA to licensed or certified technicians.

When more technologically advanced methods are unavailable in field settings, anthropometric measurements of body size can be performed, such as body mass index (BMI), waist circumference (WC) or hip circumference (HC), and skinfold thickness. Although calculation of BMI is a simple method commonly used in large-scale epidemiological research, BMI is limited in value because it is an assessment of body weight relative to height and not of body composition per se. Furthermore, the accuracy of these methods (i.e., WC, HC, and skinfold thickness measurements) may depend heavily upon repeated training of the research staff in order to obtain accurate and reliable assessments. Further limiting these anthropometric indices, the relationship between each of these measures and body composition varies tremendously by age, sex, and race/ethnicity. Additionally, these anthropometric measures (BMI, WC, and HC) are only moderately correlated with adiposity, and are weakly correlated with changes in body composition over time. As such, improved methods that allow for accurate and portable measurement of body composition could be of tremendous value for practitioners in sport performance, commercial fitness, or allied health care fields.

Most recently, three-dimensional body scanning systems have been developed and provide accurate estimates of body volume; however, the cost of these devices and their inability to be transported also limit their use for many practical settings and field assessments. There is currently no smartphone/tablet application that can estimate body composition from a single two-dimensional image.

Accurate methods to measure and track changes in aerobic fitness are not readily available to consumers. For example, the relevant equipment in exercise physiology laboratories for measuring oxygen consumption and heart rate are too expensive for individual and commercial use. Furthermore, precise testing protocols often require an individual to exercise to a point of maximal exhaustion, and hence, high subject motivation is needed. Additionally, subjects are required to breathe into a tube connected to a metabolic analyzer while wearing a nose clip, which is very uncomfortable.

Assessing aerobic fitness using a graded exercise test is the gold standard measure of $VO_2$ max, and conventionally it requires a difficult process to determine. The term $VO_2$ max refers to the maximum rate of oxygen uptake by the body during exercise, and is commonly expressed in 3 different indices. This measure of $VO_2$ max can be expressed in absolute terms, as liters of oxygen per minute (L/min). A conventional method expresses $VO_2$ max relative to body weight (milliliters of oxygen uptake per kilogram of body weight per minute (ml/kg/min)), which is more strongly correlated with athletic performance in weight-bearing activities such as walking or running. Another common method expresses $VO_2$ max relative to Fat-Free Mass (FFM) (milliliters of oxygen uptake per kilogram of FFM per minute (ml/kg of FFM/min)), which more accurately describes the changes in aerobic fitness or "training status" due to exercise, independent of any changes in body weight.

Field tests are available that accurately predict aerobic fitness from a timed run over a given distance. Though these tests are simpler than laboratory testing, limitations exists that prevent widespread usage. For example, an individual must know the exact distance, have a precise timing mechanism, and understand how to use the necessary prediction equations (i.e., how to calculate aerobic fitness based on variables such as time, distance, heart rate, etc.).

Very little mobile technology exists to determine the effectiveness of exercise and nutrition programs.

It is with respect to these and other considerations that the various aspects and embodiments of the present disclosure are presented.

SUMMARY

Body composition is estimated from a single two-dimensional (2D) image. In an embodiment, anatomical dimensions are measured, in the form of linear measurements, from a single 2D image that is taken from the front/anterior view or from the rear/posterior view. The linear measurements are used to estimate the body volume of the individual. Total body density is calculated from estimated body volume and body weight (more precisely, body mass). Body composition (fat mass and fat-free mass) of the individual is derived from the body density using known mathematical conversion formulas. According to some implementations, the image is a digital image and the digital image is obtained using a mobile, handheld communication device.

Systems and methods are provided that determine an individual's fitness by determining body composition of the individual using a picture of the individual, determining the individual's $VO_2$ max based on the individual's movement (e.g., walking and/or running a measured distance over a measured amount of time), and determining the individual's fitness based on the body composition and the determined $VO_2$ max.

An implementation comprises a method of determining fitness of an individual, the method comprising: determining a body composition assessment of an individual; determining a $VO_2$ max of the individual; determining a fitness of the individual using the body composition assessment and the $VO_2$ max; and outputting the fitness.

An implementation comprises a system of determining fitness of an individual, the system comprising: an image capture device; and a computing device configured to: determine a body composition assessment of the individual using a body composition assessment module; determine a $VO_2$ max of the individual using a $VO_2$ max determination module; and determine a fitness of the individual using a fitness determination module using the body composition assessment and the $VO_2$ max.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Figure 1:
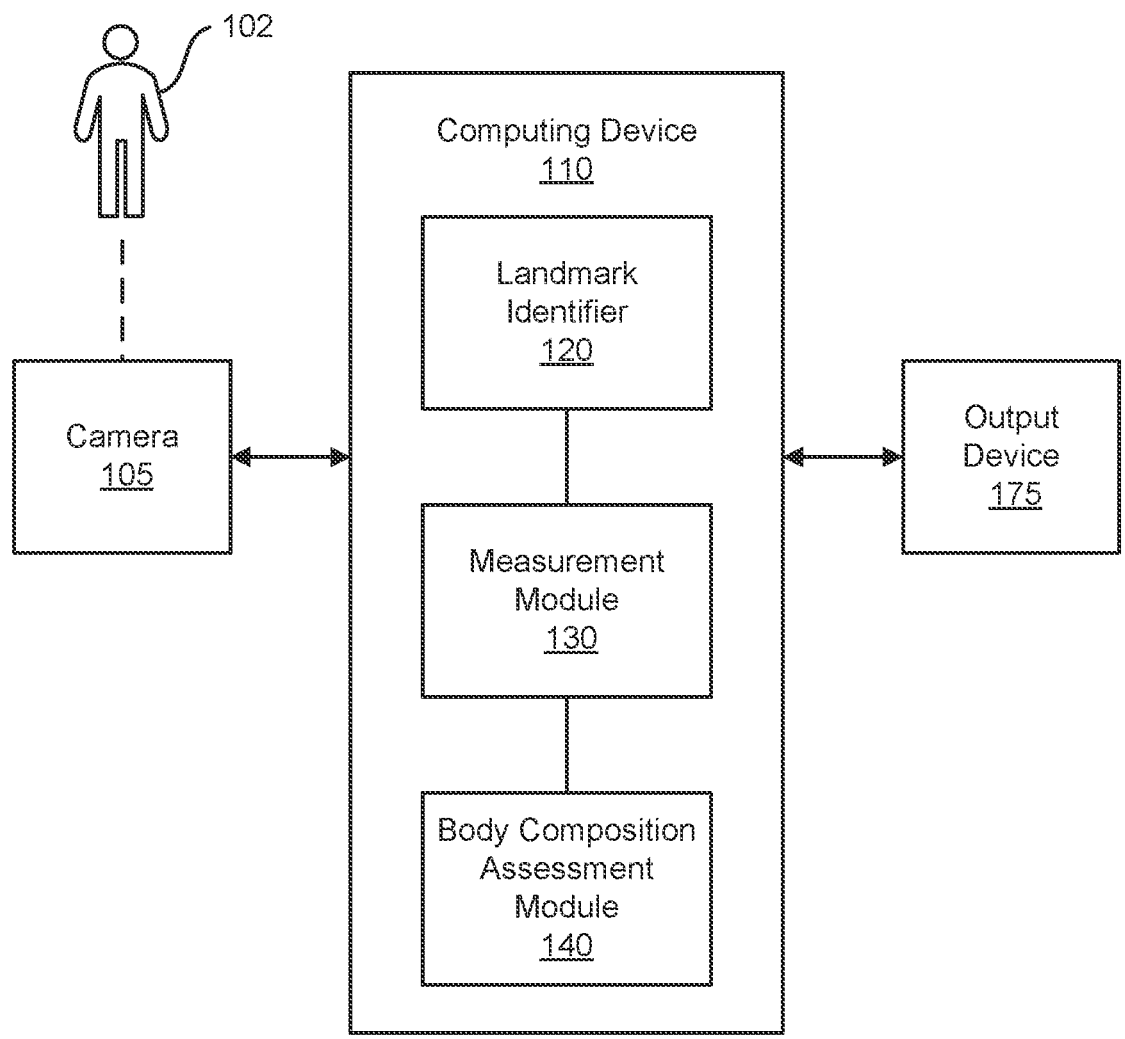
FIG. 1 is an illustration of an exemplary environment for body composition assessment using two-dimensional (2D) digital image analysis.

This description provides examples not intended to limit the scope of the appended claims. The description is not to be taken in a limiting sense, but is made merely for the purpose of illustrating the general principles of the invention, since the scope of the invention is best defined by the appended claims. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present in all embodiments described herein.

Various inventive features are described herein that can each be used independently of one another or in combination with other features.

FIG. 1 is an illustration of an exemplary environment 100 for body composition assessment using two-dimensional (2D) digital image analysis. As described further herein, a single digital two-dimensional image of an individual 102 is used. In some implementations, the 2D image is taken from the anterior (front) view. In other implementations, the 2D image may be taken from the posterior (rear) view. The individual 102 may take the 2D image using a camera 105, or another user or administrator may take the 2D image of the individual 102. The body volume of the individual 102 is estimated by measuring the diameter of one or more anatomical landmarks from the single 2D image. In some implementations, the body volume of the individual 102 is estimated by measuring the diameter of a plurality (e.g., two, three, etc.) anatomical landmarks from the single 2D image, such as the shoulders, waist, and/or hips, although the invention is not limited thereto.

The environment 100 may include the camera 105, a computing device 110, and an output device 175 in communication with each other through a network. The network may be a variety of network types including the public switched telephone network (PSTN), a cellular telephone network, and a packet switched network (e.g., the Internet). Alternately, the camera 105 and/or the output device 175 may be comprised within the computing device 110. Although only one camera 105, one computing device 110, and one output device 175 are shown in FIG. 1, there is no limit to the number of cameras 105, computing devices 110, and output devices 175 that may be supported.

The camera 105 may comprise, or be embodied in, any image capturing device, system, or apparatus. The output device 175 may comprise any device, system, or apparatus for providing a result (e.g., a body composition assessment described further herein) received from the computing device 110 to a user, a storage device, a display, etc.

Figure 8:
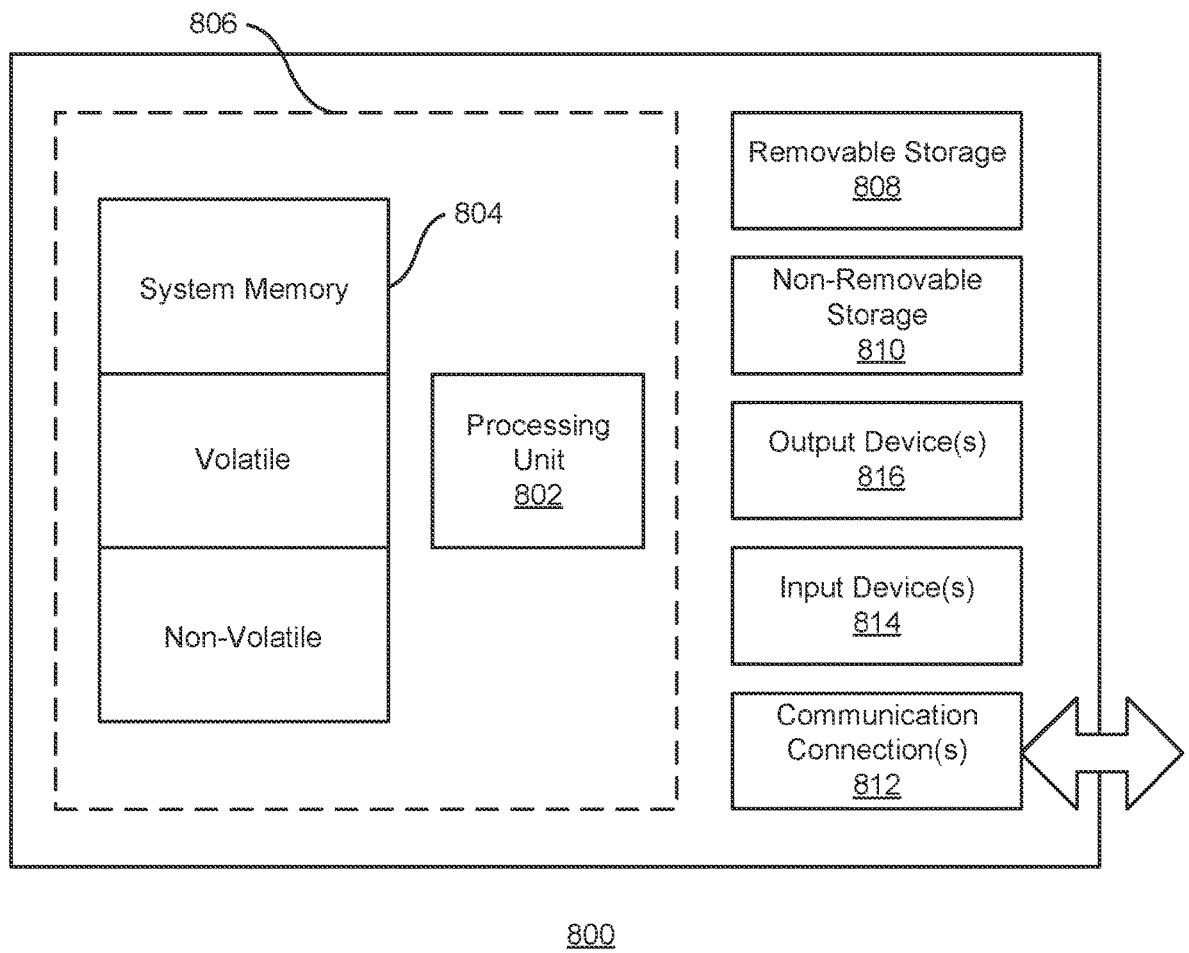
FIG. 8 shows an exemplary computing environment in which example embodiments and aspects may be implemented.

The computing device 110 may be implemented using a variety of computing devices such as handheld communication devices, smart phones, desktop computers, laptop computers, tablets, and video game consoles. Other types of computing devices may be supported. A suitable computing device is illustrated in FIG. 8 as the computing device 800.

The computing device 110 may include a landmark identifier 120, a measurement module 130, and a body composition assessment module 140.

The landmark identifier 120 receives a two-dimensional (2D) image of an individual 102 (e.g., taken and/or provided by the camera 105) and identifies one or a plurality of anatomical landmarks of the image. The anatomical landmarks may include hips, waist, overarms, shoulders, neck, knees, etc. Although the embodiments described herein are directed to identifying and using a plurality of landmarks, such as three anatomical landmarks (e.g., hips, waist, shoulder), the invention is not limited thereto, and any number of anatomical landmarks, as well as any anatomical landmarks, are contemplated. As the number of anatomical landmarks used is increased, the assessments herein may become more accurate. It is contemplated that the hips, waist, and shoulders are straightforward to accurately identify and measure in a 2D image.

The measurement module 130 receives the identified anatomical landmark information from the landmark identifier 120 and measures the linear distance of the diameter of the individual at these anatomical landmarks. The linear distance may be in inches, centimeters, or pixels, depending on the implementation, although any unit(s) of linear distance measurement may be used. The linear distances determined by the measurement module 130 are then used to estimate the body volume of the individual 102, as described further herein.

The estimated body volume from the measurement module 130 is provided to the body composition assessment module 140. The body composition assessment module 140 uses the estimated body volume (as well as the body mass in some embodiments) to determine a body composition assessment (e.g., using body volume in some embodiments) as described further herein. The body composition assessment is then provided to the output device 175 for output to a user, to storage, to a display, etc.

In an implementation, the computing device 110 is provided for measuring the anatomical dimensions of the human body. The computing device 110 may be a mobile device, and/or configured to provide a digital anthropometer on a mobile device, and to digitize anatomical landmarks on a displayed image such as a photograph (such as a single 2D digital image) of the human body displayed on the computing device 110 (or the camera 105) with established calibration methods for measuring dimensions of the human body.

The measurement module 130 may be configured to measure the dimensions of the human body and may comprise a programmed device including a digital display, an automated image analysis program to measure an array of pixels and a camera (such as the camera 105) for acquiring an image of a person (e.g., the individual 102) on the digital display, and means for digitizing anatomical landmarks on an image of the person on the display for measuring dimensions of the human body.

The measurement module 130 enables the ability to derive the anatomical measurement such as the linear measurement from the front/anterior aspect of the body (or the rear/posterior aspect of the body), and to then calculate an estimate of total body volume using mathematical equations. The calculated body volume is converted by the body composition assessment module 140, to body composition (fat mass and fat-free mass) using known mathematical conversion equations.

The body composition assessment module 140 uses a prediction model which can estimate total body volume with near perfect precision across a wide range of body sizes, which is then converted to body fat percentage, fat mass, and fat-free mass after accounting for the total mass/body weight of the individual. The methodology is strongly correlated with the criterion measure of total body volume as measured by UWW (r=0.999), as well as three known other methods of estimating total body volume using DXA (e.g., r=0.999, 0.998, and 0.997), for example.

Once an image is obtained and digitized by the camera 105 and/or the computing device 110, digitization points on anatomical landmarks for purpose of body composition measurements can be performed by the landmark identifier 120. The invention may be utilized in commercial fitness, athletic performance, and allied health care settings to measure body dimensions, shape, and body composition based on anatomical ratio relationship, and to track progress of these measurements over time. The anthropometric measurements can be acquired from a single digital image of the individual 102.

Figure 2:
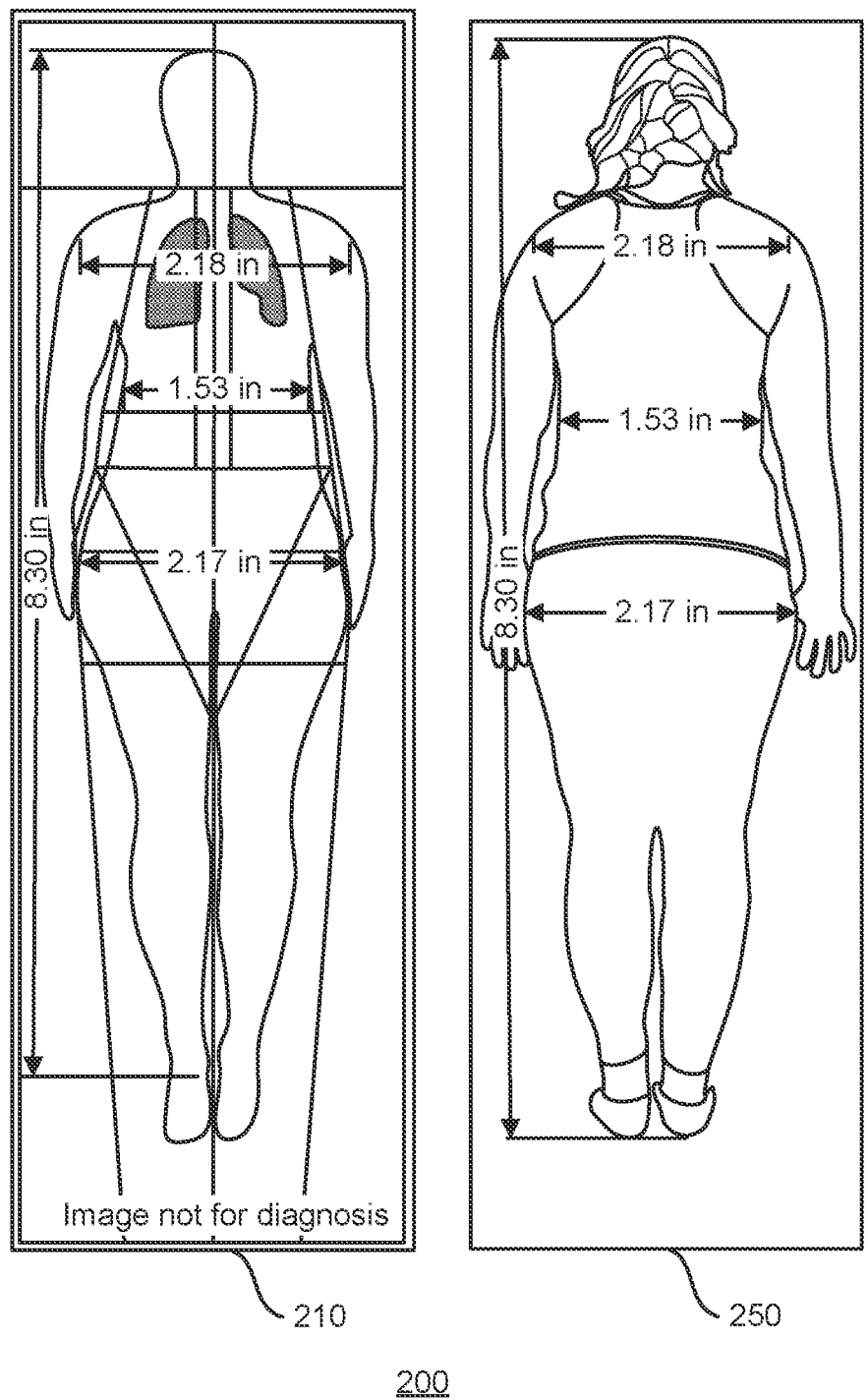
FIG. 2 is an illustration of example image of a subject obtained using dual energy x-ray absorptiometry (DXA) and an associated 2D digital image for body composition assessment using a camera according to an implementation of the invention.

FIG. 2 is an illustration 200 of an example image 210 of a subject obtained using dual energy x-ray absorptiometry (DXA) and an associated 2D digital image 250 for body composition assessment using a camera according to an implementation of the invention. Thus, while DXA techniques use a specialized image 210 of the subject, the techniques of the invention described herein can use a photo of the subject taken from an anterior (front) view or a posterior (rear) view, such as a 2D digital image 250 taken with a camera such as a camera integrated with a handheld computing device like a phone or a tablet.

Figure 3:
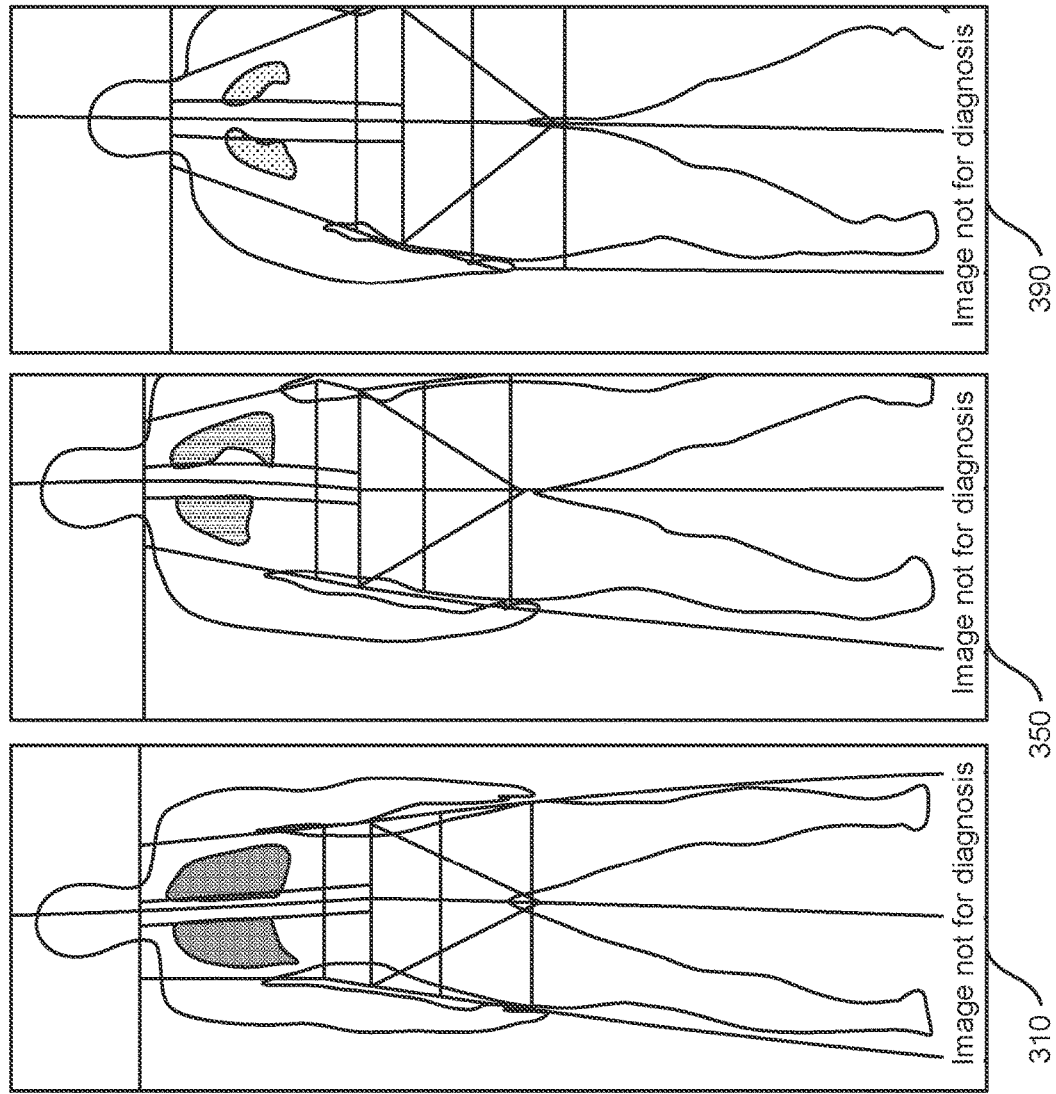
FIG. 3 is an illustration of example images obtained using a DXA machine.

FIG. 3 is an illustration 300 of example images 310, 350, 390 obtained using a DXA machine. The images 310, 350, 390 correspond to subjects whose body composition assessment cannot be performed by a DXA technique because of the body size. For example, the image 310 corresponds to a subject whose body is too tall for DXA techniques, and image 350 corresponds to a subject whose body is too muscular and wide for DXA techniques, and the image 390 corresponds to a subject whose body is too large for DXA techniques. The techniques of the invention described herein, however, can be used for all body sizes and shapes, including those of the subjects having the images 310, 350, 390.

In some implementations, patient information (age, sex, race/ethnicity) as well as body weight (i.e., mass) and height are obtained and used for normalizing the individual's height in the digital image, and determining a pixel to distance ratio using the acquired patient information and the normalized patient height.

Thus, in some implementations, a front/anterior perspective image of the individual is obtained using a mobile, handheld communication device, which on one side has a screen capable of displaying a front/anterior image of the individual 102 being viewed with a camera or image capture device on an opposite side. Mobile, handheld communication devices capable of running a program in accordance with the invention could be used, such as iPhone®, iPod Touch®, iPad® and Android® devices including tablets and Windows® based tablets.

Figure 4:
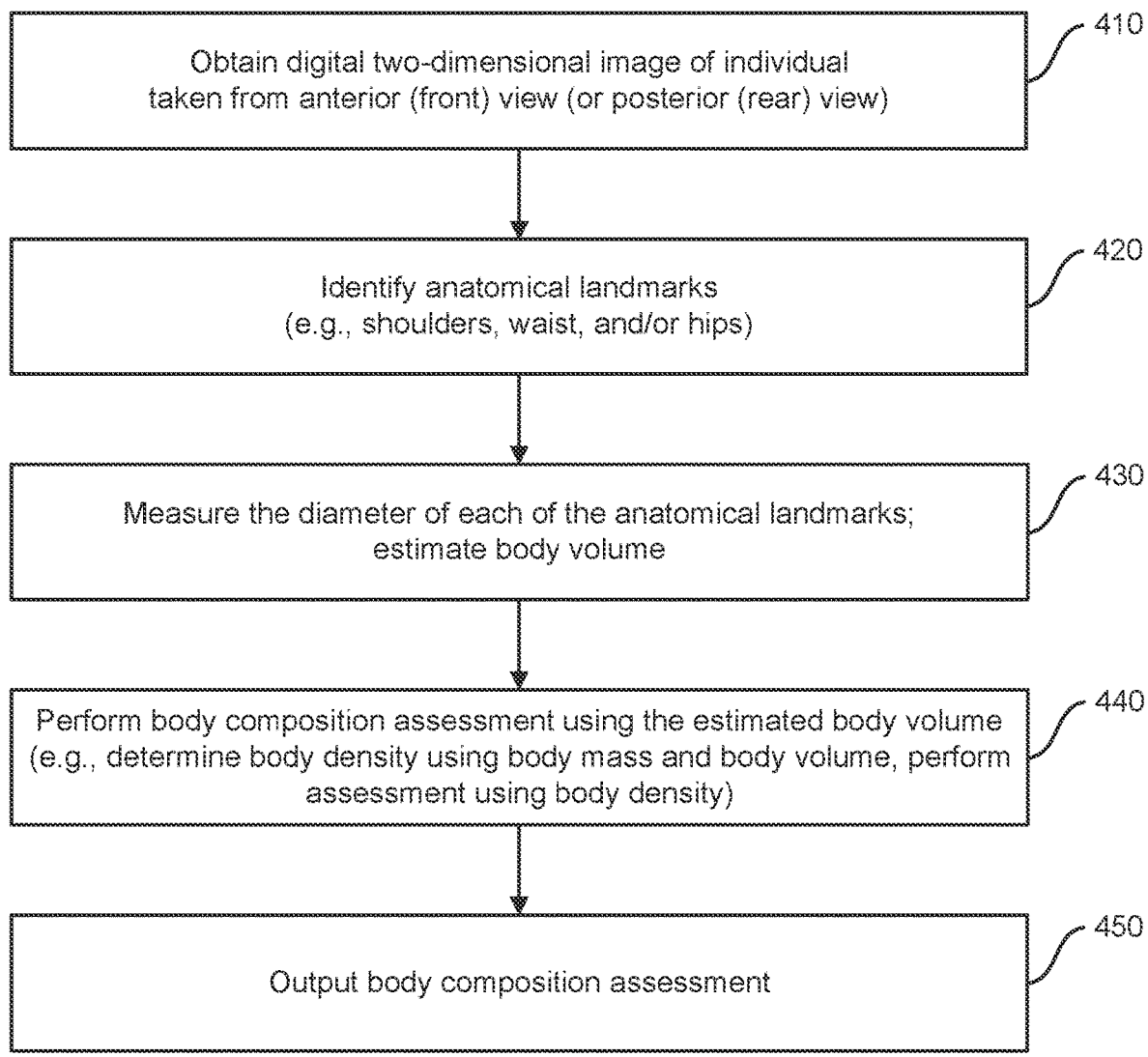
FIG. 4 is an operational flow of an implementation of a method for body composition assessment using 2D digital analysis.

A method of estimating body composition from a single 2-dimensional digital image is provided using a series of anatomical landmarks with near perfect accuracy (r=0.999) when compared to conventional methods such as underwater weighing (UWW). FIG. 4 is an operational flow of an implementation of a method 400 for body composition assessment using 2D digital analysis. The method 400 may be implemented using the computing device 110, alone or in conjunction with the camera 105 and/or the output device 175.

At 410, a digital two-dimensional image of an individual, such as the individual 102, is obtained, e.g., by the camera 105 and/or the computing device 110. In some implementations, the image is taken from the anterior (front) view, while in other implementations, the image is taken from the posterior (rear) view. In some implementations, the digital image used is taken from the front/anterior view or the rear/posterior view using a mobile, handheld communication device.

At 420, anatomical landmarks are identified in the 2D digital image, e.g., by the landmark identifier 120. The anatomical landmarks may comprise shoulders, waist, and/or hips in some implementations, although any anatomical landmarks may be used and although any number of anatomical landmarks may be used. In some implementations, a digital anthropometer on a mobile device is used to identify anatomical landmarks on the digital image.

At 430, the diameter of each of the anatomical landmarks is measured and the body volume is estimated, e.g., by the measurement module 130. Linear measurements may be obtained in some implementations, and then used to estimate the body volume of the individual. In some implementations, the diameters (i.e., the linear measurement across the individual's body in the image at the landmarks) are converted to ratios by dividing those diameters by the individual's height. These ratios may then be used in an equation to obtain the body volume estimate. An example equation using shoulders, waist, and hips is given by Equation (1):

$$\text{Body Volume(Liters)} = \text{Hip Diameter}_{Adjusted} + \text{Waist Diameter}_{Adjusted} + \text{Shoulder Diameter}_{Adjusted} + \text{Body Mass}_{kg} + \text{Height}_{cm} \quad (1)$$

It is noted that one or more of the values of this equation, as well as the equations below, may be adjusted with a "slope" or variable, depending on the implementation, which may weight or otherwise adjust the particular value. In this manner, the parameters of the equation (e.g., hip diameter, waist diameter, shoulder diameter, body mass, and height) may be accounted for and their units standardized or normalized.

Another example equation is given by Equation (2):

$$\text{Body Volume (Liters)} = \left(\text{Height}_{cm}\left(\frac{\text{Image Hip Diameter}}{\text{Image Height}}\right)\right) + \left(\text{Height}_{cm}\left(\frac{\text{Image Waist Diameter}}{\text{Image Height}}\right)\right) + \left(\text{Height}_{cm}\left(\frac{\text{Image Shoulder Diameter}}{\text{Image Height}}\right)\right) + \text{Body Mass}_{kg} + \text{Height}_{cm} \quad (2)$$

Another example equation is given by Equation (3):

$$\text{Body Volume (Liters)} = \left(A \times \left(\text{Height}_{cm} \times \left(\frac{\text{Image Hip Diameter}}{\text{Image Height}}\right)\right)\right) + \left(B \times \left(\text{Height}_{cm} \times \left(\frac{\text{Image Waist Diameter}}{\text{Image Height}}\right)\right)\right) + \left(C \times \left(\text{Height}_{cm} \times \left(\frac{\text{Image Shoulder Diameter}}{\text{Image Height}}\right)\right)\right) + (D \times (\text{Body Mass}_{kg})) + (E \times (\text{Height}_{cm})) + F. \quad (3)$$

In Equation (3), variables A, B, C, D, and E, are included as "slopes," and F is included as an "intercept," which may be determined and adjusted as desired to tune or create a final outcome of the body volume. The values for variables A, B, C, D, E, and F may be determined experimentally and/or using numerical and/or mathematical techniques such as multivariate linear regression.

At 440, the body composition assessment is performed using the estimated body volume. The body composition assessment may be performed by the body composition assessment module 140. In some embodiments, total body density is calculated from estimated body volume and body weight. Body composition (fat mass and fat-free mass) of the individual is then derived from density using known mathematical conversion formulas, such as the Siri equation which converts body density (BD) in percent body fat (% BF). Other conversion formulas and techniques can be used. In some embodiments, measurements are taken from the image concerning the torso and hips, as well as the body weight, to assess body composition.

At 450, the body composition assessment is outputted. The computing device 110 may output the body composition to an associated output device, such as the output device 175.

In this manner, the systems, methods, and techniques described herein are cost effective, can accommodate dimensions of taller and/or heavier individual, and do not rely on trained personnel or staff.

In some implementations, a programmed device is provided that includes an automated analysis of arrays of pixels, a camera for acquiring a digital image of a person, and means for automatically identifying a series of anatomical landmarks on an image of an individual. The number of pixels is determined using an automated program to measure the linear distance at a series of anatomical landmarks, and the prediction equation includes measurements of the hip, waist, and overarm diameter, standardized to the height of the individual.

In some implementations, the present invention includes a means of acquiring an image of a person, a method of deriving body volume and body composition estimates from a programmed smartphone application which uses an automatic image analysis program, digitizing points on a plurality of anatomical landmarks on the displayed image, determining linear anatomical dimensions of the person's body using the digitized points and a scale factor for the displayed image, and making an anatomical prediction using the determined linear anatomical dimensions.

Some implementations comprise acquiring a single image of the person obtained from the front/anterior view, digitizing points on anatomical landmarks on each displayed image and determining linear anatomical dimensions of the person's body (in pixels) using the digitized points and a scale factor (adjusted to the person's height in pixels) for each displayed image for making the anatomical prediction.

In some implementations, a body volume and body composition assessment method comprises acquiring an image of an individual on a display screen having an array of pixels, determining a pixel to distance ratio for the displayed image, and calculating the body composition of the individual using the cross-sectional diameter (linear distance) of the individual at a series of anatomical landmarks (hips, waist, and shoulders). A known linear distance in the displayed image and the number of display screen pixels spanning the distance are used in determining pixel to distance ratio. The known linear distance used in the estimation equation is the height of the individual.

The body composition assessment method in example images further includes scaling the size of the image relative to the display screen to normalize the known linear distance in the image to a display screen reference distance corresponding to a known number of pixels for determining the pixel to distance ratio.

The person performing the screening can operate an image capture device of a camera for acquiring the image of the patient. A single two-dimensional camera providing a 2D image can be used. The method preferably includes leveling the image capture device before capturing the image from which the pixel to distance ratio is to be determined for eliminating distortion. The image capture device and display screen are part of a mobile, handheld communication device.

The development of a smartphone/tablet application that can accurately measure body composition from a single 2D image would have tremendous appeal for practitioners in the allied health field, in research settings, and in recreationally active individuals to provide a single estimate for diagnostic purposes, and to monitor changes in body composition over time. In addition, the utility of a portable body composition assessment method would provide tremendous value for practitioners or clinicians in rural health community health outreach programs when access to more technologically advanced body composition assessment methods are unavailable.

Embodiments contemplated herein, which provide an accurate method of assessing body composition, may be implemented via a smartphone/tablet application. Various embodiments and implementations provide portable, accurate, non-invasive body composition measurement available for use in allied health and clinical settings, the commercial fitness industry, and fitness enthusiasts, for example, though it is not limited thereto. There is potential for the embodiments and implementations in the health and fitness industry. Commercial fitness centers need accurate methods of body composition assessment of their patrons. In addition, the embodiments and implementations would be of interest to fitness enthusiasts interested in measuring their own body composition and tracking changes due to their exercise training program. Embodiments and implementations accurately measure changes in weight and body composition through the least obtrusive means possible. Monitoring changes in body composition through an application would be a desired addition by users that may already use a health and fitness application.

The methodology may be limited, as are the UWW and BodPod techniques, because these methods do not account for total body water or bone mineral content. As a result, body composition can only be separated in to two components, fat mass and fat-free mass. Because bone mass does not change acutely as a result of exercise training, and because this method will not be used as a diagnostic or screening tool for osteoporosis or low bone mass, accounting for bone mass would be of little value for the embodiments and implementations contemplated herein. In addition, although this methodology (as well as UWW and BodPod) does not account for total body water, this is also of little value to for the embodiments and implementations contemplated herein. An additional limitation of the methodology is that the image is taken of the front of the body with hips and shoulders parallel to the camera, with the camera held directly at hip, eye, or chest level to allow for identification of all of the anatomical points of interest (as shown in FIGS. 2 and 3 for example). An image taken with an individual wearing loose-fitting clothing, or taken at an angle may distort the perspective of the image and add potential error to the estimate of body composition.

An accurate method of assessing body fat is with a system called a multi-compartment model. Basically, the more "compartments" (or tissues) of the body that are measured, the better the estimate of fat will be. A common multi-compartment approach is to measure the following compartments: body volume, total body water, and body weight. Once each of these compartments are measured, the values are entered into an existing regression/prediction equation that provides the outcome measure of fat mass.

Body weight is easily measured with a standard scale. In the lab, body volume is measured with sophisticated methods of either underwater weighing or x-ray. However, the smartphone applications (apps) described or otherwise contemplated or provided herein estimate body volume, and provide nearly perfect agreement compared to the other laboratory methods.

Total body water is not measured with the app(s), but instead can be done with a process called bioelectrical impedance analysis (BIA) or bioelectrical impedance spectroscopy (BIS). Scales in retail stores that supposedly measure body fat percentage are not very accurate, but use the BIA method. It is a process of sending an unnoticeable electrical current(s) through the body from one "pole" to another. In the case of the scales, the feet serve as the poles. With more advanced methods, the poles are surface sticky electrodes that are placed over the hand(s) and foot (feet). The measures are performed while the person lays on their back, face up.

In some implementations, the smartphone application(s) can be used with bioelectrical impedance (BIA or BIS) and a weighing scale to provide a multi-compartment model for measuring body fat. This process is more user friendly than putting someone in a tank of water to measure body volume, and then performing the other measures of bioimpedance and body weighing.

In some implementations, the process uses the smartphone app(s) plus (any) bioelectrical impedance analyzer and (any) weighing scale for a multi-compartment modeling method of fat determination.

In some implementations, a system for measuring total body water can be coupled with a process of body volume from an image.

Using the determined body composition of an individual, and a determination of the individual's $VO_2$ max (i.e., maximal oxygen consumption), the individual's fitness may be determined.

Figure 5:
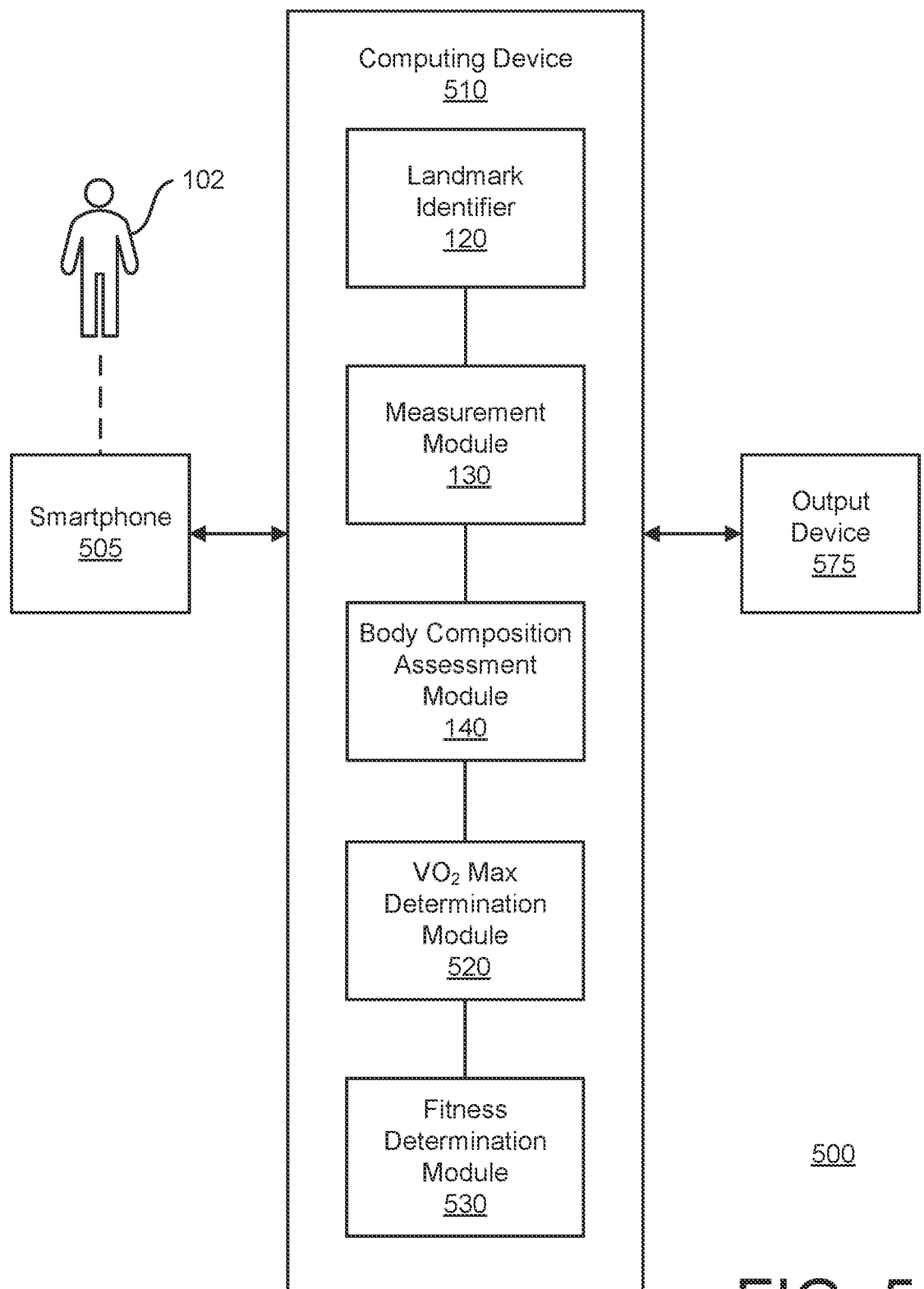
FIG. 5 is an illustration of an exemplary environment for fitness determination of an individual.

FIG. 5 is an illustration of an exemplary environment 500 for fitness determination of an individual. Similar to described above with respect to FIG. 1, for example, a body composition assessment is performed using a single digital 2D image of the individual 102 is used. In some implementations, the 2D image is taken from the anterior (front) view. In other implementations, the 2D image may be taken from the posterior (rear) view. The individual 102 may take the 2D image using a camera incorporated into a smartphone 505, or another user or administrator may take the 2D image of the individual 102. Operations similar to those described above with respect to FIGS. 1-4 may be used, depending on the implementation, to determine and output a body composition assessment, e.g. from the body composition assessment module 140, to the output device 575, the smartphone 505, and/or the fitness determination module 530.

The environment 500 may include the smartphone 505 (which may include a camera such as the camera 105 described above with respect to FIG. 1, for example, depending on the implementation), a computing device 510, and an output device 575 in communication with each other through a network. The network may be a variety of network types including the public switched telephone network (PSTN), a cellular telephone network, and a packet switched network (e.g., the Internet). Alternately, the smartphone 505 and/or the output device 575 may be comprised within the computing device 510. Although only one smartphone 505, one computing device 510, and one output device 575 are shown in FIG. 5, there is no limit to the number of smartphones 105, computing devices 510, and output devices 575 that may be supported.

The smartphone 505 may comprise, or be embodied in, any image capturing device, system, or apparatus. The smartphone 505 may also comprise one or more modules and/or applications to monitor an individual's movements (e.g., walking, running, distance measurement, etc.) over an amount of time (e.g., seconds, minutes, hours, days, etc.).

The output device 575 may comprise any device, system, or apparatus for providing a result (e.g., a fitness determination, a $VO_2$ max determination, and/or a body composition assessment described further herein) received from the computing device 510 to a user, a storage device, a display, etc.

The computing device 510 may be implemented using a variety of computing devices such as handheld communication devices, smart phones, desktop computers, laptop computers, tablets, and video game consoles. Other types of computing devices may be supported. A suitable computing device is illustrated in FIG. 8 as the computing device 800.

The computing device 510 may include a landmark identifier 120, a measurement module 130, and a body composition assessment module 140. These modules are similar to those described above with respect to FIG. 1 and their descriptions are omitted here for brevity.

The computing device 510 may also include a $VO_2$ max determination module 520 and a fitness determination module 530.

The $VO_2$ max determination module 520 receives data from the smartphone 505 that can be used to determine $VO_2$ max. The data may include the distance that the individual 102 moved (e.g., by walking, running, etc.) in a measured amount of time. The $VO_2$ max determination module 520 uses this data to determine $VO_2$ max for the individual 102. The $VO_2$ max for the individual 102 can be provided as output to the output device 575 or to the smartphone 505. Additionally or alternatively, the $VO_2$ max for the individual 102 can be provided as output to the fitness determination module 530.

The fitness determination module 530 receives as input the body composition assessment (from the body composition assessment module 140) and the $VO_2$ max (from the $VO_2$ max determination module 520), and uses these inputs in determining a fitness determination. The fitness determination may then be provided as output from the fitness determination module 530 (or the computing device 510) to the smartphone 505 and/or the output device 575, depending on the implementation.

Figure 6:
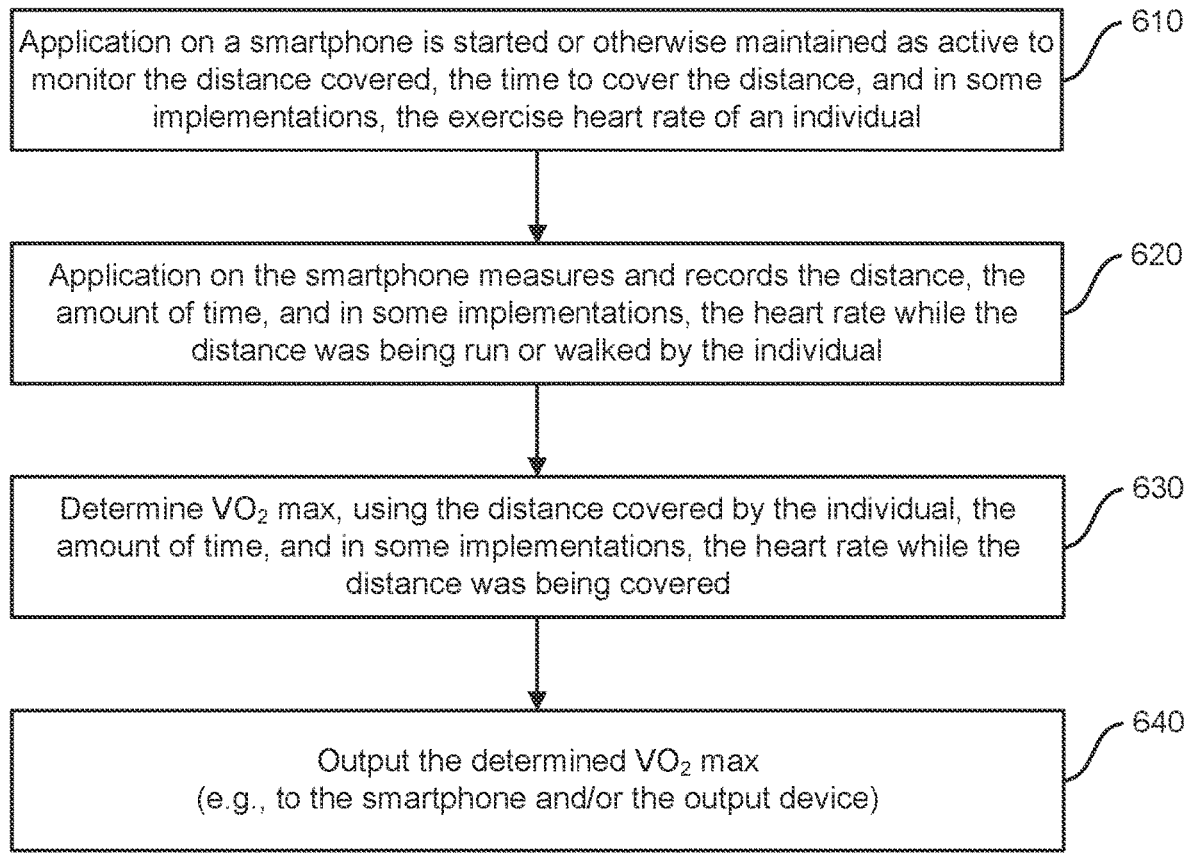
FIG. 6 is an operational flow of an implementation of a method for $VO_2$ max assessment.

FIG. 6 is an operational flow of an implementation of a method 600 for $VO_2$ max assessment. The method tracks a given distance in which an individual runs and/or walks and the time to complete such distance. From these variables (i.e., time and distance), the system will automatically calculate $VO_2$ max as soon as the individual completes the run/walk test.

At 610, an application on a smartphone (e.g., the smartphone 505 of the individual 102 who is being tested) is started or otherwise maintained as active to monitor the distance covered, the time to cover the distance, and in some implementations, the exercise heart rate.

At 620, the individual (while carrying the smartphone or having the smartphone attached to the individual) runs or walks a given distance in an amount of time. The application on the smartphone measures and records the distance, the amount of time, and in some implementations, the heart rate while the distance was being run or walked. Distance may be tracked and measured using a global positioning system (GPS), in some implementations. The system may have the option, in some implementations, of the individual wearing a heart rate monitor connected via Bluetooth to the smartphone 505.

At 630, the application uses an algorithm (or other process or technique), which may be comprised within the $VO_2$ max determination module 520 in some implementations, to determine $VO_2$ max, using the distance covered by the individual, the amount of time, and in some implementations, the heart rate while the distance was being covered. Thus, in some implementations, the smartphone 505 application will track distance, record time, and automatically calculate predicted $VO_2$ max upon completion of the run or walk.

This overcomes the limitations of field-testing by creating an automated process that will track a given distance in which an individual runs and/or walks and the time to complete such distance. From these variables (i.e., time and distance), the system will automatically calculate $VO_2$ max as soon as the individual completes the run/walk test.

At 640, the determined $VO_2$ max is output, e.g., to the smartphone 505 and/or the output device 575.

The development of a smartphone/tablet application that can accurately measure aerobic fitness from running or walking a given distance has tremendous appeal for consumers, as well as researchers and clinicians. It provides a convenient method of measuring aerobic fitness, which is one of the most important predictors of cardiovascular health.

It is contemplated that changes in aerobic fitness may be monitored and tracked over time, as the individual is tested through the application multiple times (e.g., weekly, monthly, etc.)

This provides the availability of a simple, portable, accurate, non-invasive aerobic fitness measurement for use in allied health and clinical settings, the commercial fitness industry, and by fitness enthusiasts.

Limitations of some implementations may include: (1) the system will only work for individuals who have both lower limbs and ambulate by walking/running, (2) the system will require carrying a smartphone, which may be burdensome for someone not accustomed to holding or carrying such a device while walking/running, and (3) the test will require walking/running on a fairly flat surface.

Figure 7:
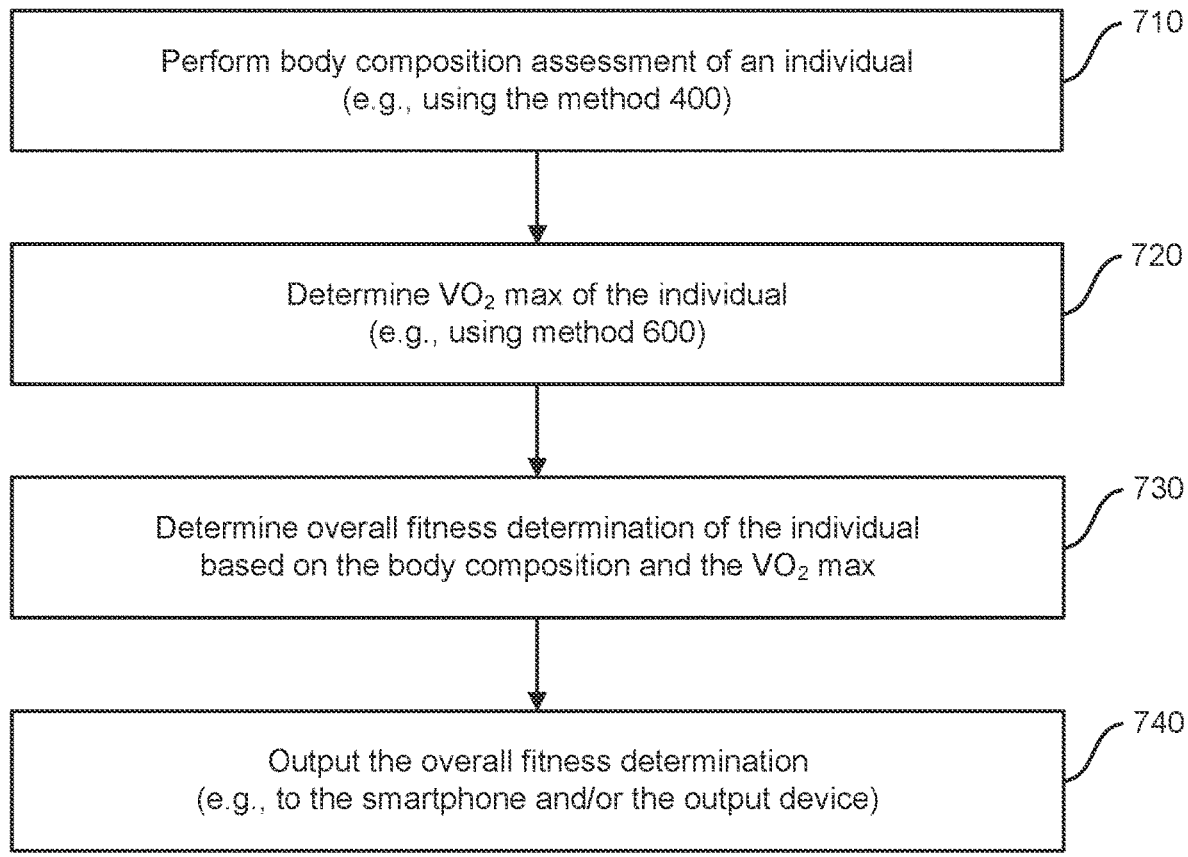
FIG. 7 is an operational flow of an implementation of a method for fitness determination.

FIG. 7 is an operational flow of an implementation of a method 700 for fitness determination. In this manner, aerobic fitness can be determined using smartphone technology from the results of a run (or walk) test.

At 710, a body composition assessment of an individual is performed, e.g., using the method 400 described above with respect to FIG. 4.

At 720, a $VO_2$ max determination for the individual is made, e.g., using the method 600 described above with respect to FIG. 6.

At 730, an overall fitness determination of the individual is made (e.g., by the fitness determination module 530) based on the body composition assessment and the $VO_2$ max determination.

At 740, the overall fitness determination is output, e.g., to the smartphone 505 and/or the output device 575.

Examples are provided of converting the results from fields tests into the expression of $VO_2$ max as ml/kg of FFM/min.

There are a number of field methods that are available to estimate $VO_2$ max from a timed walk/run. For some methods, the distance that is covered within a certain time period is used as the prediction variable. The Cooper 12 minute run is an example. For this method, a person runs or walks as far possible within a 12 minute period. The distance covered is recorded in meters and is placed into the following equation: $VO_2$ max ml/kg/min=(Distance in Meters-504.9)/44.73.

Other methods require the participant to run or walk over a given distance and the time completed the distance is used as the prediction variable. For example, the 1.5 mile run/walk is common technique that uses the following equation: $VO_2$ max ml/kg/min=(483/time to complete the distance in minutes)+3.5.

The methods, such as the two examples here, can predict $VO_2$ max expressed relative to a person's body weight, with the units mentioned above (ml/kg/min). This is then converted to ml/kg of FFM/min with the following steps: Multiply ml/kg/min by body weight in kilograms to convert to ml/min. Then, divide ml/min by fat-free mass in kilograms to convert to ml/kg of FFM/min.

The processes described herein are cost effective, easy to use, portable, and non-invasive.

FIG. 8 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 8, an exemplary system for implementing aspects described herein includes a computing device, such as computing device 800. In its most basic configuration, computing device 800 typically includes at least one processing unit 802 and memory 804. Depending on the exact configuration and type of computing device, memory 804 may be volatile (such as random access memory (RAM)), non-volatile (such as read-only memory (ROM), flash memory, etc.), or some combination of the two. This most basic configuration is illustrated in FIG. 8 by dashed line 806.

Computing device 800 may have additional features/functionality. For example, computing device 800 may include additional storage (removable and/or non-removable) including, but not limited to, magnetic or optical disks or tape. Such additional storage is illustrated in FIG. 8 by removable storage 808 and non-removable storage 810.

Computing device 800 typically includes a variety of computer readable media. Computer readable media can be any available media that can be accessed by the device 800 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 804, removable storage 808, and non-removable storage 810 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 800. Any such computer storage media may be part of computing device 800.

Computing device 800 may contain communication connection(s) 812 that allow the device to communicate with other devices. Computing device 800 may also have input device(s) 814 such as a keyboard, mouse, pen, voice input device, touch input device, etc. Output device(s) 816 such as a display, speakers, printer, etc. may also be included. All these devices are well known in the art and need not be discussed at length here.

In an implementation, a method of determining fitness of an individual comprises: determining a body composition assessment of an individual; determining a $VO_2$ max of the individual; determining a fitness of the individual using the body composition assessment and the $VO_2$ max; and outputting the fitness.

Implementations may include some or all of the following features. Determining the body composition assessment of the individual comprises: obtaining an image of the individual; measuring a cross-sectional diameter (linear distance) at a plurality of anatomical landmarks on the image of the individual; estimating a body volume of the individual; and estimating a body composition of the individual using the estimated body volume. Obtaining the image comprises at least one of: capturing a digital image of the individual, capturing a profile image from the front/anterior angle or the rear/posterior angle, capturing the image of the individual using a mobile, handheld communication device, or receiving the image from a storage device, an image capture device, a camera, or a smartphone. The plurality of anatomical landmarks comprises at least one of the hips, the waist, or the shoulders, and wherein measuring the cross-sectional diameter (linear distance) at the plurality of anatomical landmarks comprises at least one of using an automated image analysis program, or adjusting for standing height. The image is a two-dimensional (2D) digital image, and wherein estimating the body volume of the individual comprises measuring the cross-sectional diameter (linear distance) at the series of anatomical landmarks and standing height from the 2D digital image, and accounting for age, sex, race/ethnicity, weight, and height. Estimating the body composition comprises at least one of: estimating fat mass and fat-free mass, estimating the body density of the individual from the estimated body volume and a weight of the individual, estimating relative adiposity (percentage fat mass, percentage fat) using a relation that directly relates percentage fat to body density, or estimating the body composition of the individual comprises estimating body volume from the age, sex, race/ethnicity, height, weight, and digital image measurements, and then calculating body composition, wherein the digital image measurements comprise adjusted hips, waist, and shoulders diameters. Obtaining the image comprises capturing a two-dimensional image of the individual from a front view or from a rear view. Determining the $VO_2$ max of the individual comprises: measuring a distance the individual walks or runs, and an amount of time to cover the distance; and determining the $VO_2$ max using the distance and the amount of time. Determining the $VO_2$ max further comprises determining a heart rate of the individual while the distance was being walked or run, and wherein determining the $VO_2$ max further uses the heart rate. The distance and the amount of time are measured using a smartphone. Outputting the fitness comprises outputting the fitness to a smartphone.

In an implementation, a system of determining fitness of an individual comprises an image capture device; and a computing device configured to: determine a body composition assessment of the individual using a body composition assessment module; determine a VO$_2$ max of the individual using a VO$_2$ max determination module; and determine a fitness of the individual using a fitness determination module using the body composition assessment and the VO$_2$ max.

Implementations may include some or all of the following features. The computing device is further configured to receive images of the individual, analyze the linear distance related to anatomical landmarks from the digital images to obtain linear measurements, estimate the body volume of the individual using the linear measurements, and determine the body composition assessment of the individual based at least in part upon the estimated volume. The image capture device is comprised within a mobile, handheld communication device, wherein the mobile, handheld communication device on one side has a screen capable of displaying a front/anterior image of the individual being viewed with a camera or the image capture device on an opposite side. The system is embodied by a smartphone. The computing device comprises a measurement module configured to estimate the body volume of the individual by measuring the cross-sectional diameter (linear distance) at a plurality of anatomical landmarks and standing height from the 2D digital image, and accounting for age, sex, race/ethnicity, weight, and height, wherein the plurality of anatomical landmarks comprises the hip, the waist, and the shoulder, wherein the computing device further comprises a body composition assessment module configured to estimate the body composition of the individual by estimating the density of the individual from the estimated volume and a body weight of the individual. The body composition assessment module is further configured to estimate the body composition of the individual by calculating the body fat percentage of the individual using a relation that directly relates body fat percentage to body density. Determining the VO$_2$ max of the individual comprises: measuring a distance the individual walks or runs, and an amount of time to cover the distance; and determining the VO$_2$ max using the distance and the amount of time. Determining the VO$_2$ max further comprises determining a heart rate of the individual while the distance was being walked or run, and wherein determining the VO$_2$ max further uses the heart rate. The distance and the amount of time are measured using a smartphone. The system further comprises: a memory that stores the body composition assessment module, the VO$_2$ max determination module, and the fitness determination module; and an output device that outputs the fitness of the individual.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

As used herein, the singular form "a," "an," and "the" include plural references unless the context clearly dictates otherwise. As used herein, the terms "can," "may," "optionally," "can optionally," and "may optionally" are used interchangeably and are meant to include cases in which the condition occurs as well as cases in which the condition does not occur.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:
1. A method of determining fitness of an individual, the method comprising:
  obtaining, via a camera sensor of a mobile device, a single two-dimensional (2D) image of the individual comprising an anterior or posterior portion of a body of the individual with hips and shoulders parallel to the camera sensor, wherein the mobile device is one of a smartphone or tablet;
  digitizing, by a processor of the mobile device, the single image of the individual into an array of pixels;
  identifying, by the processor and using a digital anthropometer on the mobile device, a plurality of anatomical landmarks in the digitized single image, including at a waist landmark, a hip landmark, and a shoulder landmark;
  measuring, by the processor and using an automated image analysis program that is configured to measure the array of pixels, a cross-sectional diameter as a linear distance of pixels in the single image at each of the plurality of anatomical landmarks;
  estimating, by the processor and using a predictive model, a body composition value of the individual based on the measured cross-sectional diameters;
  determining, by the processor, a VO$_2$ max of the individual based on a measured heart rate of the individual while walking or running a distance over an amount of time;

determining, by the processor, a fitness value of the individual using the determined body composition value and the determined $VO_2$ max, wherein the fitness value is indicative of the individual's aerobic fitness and/or cardiovascular health; and outputting, by the processor, the fitness value to a display of the mobile device via an application executing on the mobile device, wherein the fitness value is used to monitor changes to the individual's aerobic fitness and/or cardiovascular health over time.

2. The method of claim 1, wherein measuring each of the cross-sectional diameters as a linear distance of pixels in the single image at each of the plurality of anatomical landmarks comprises adjusting for standing height.

3. The method of claim 1, wherein estimating the body composition value of the individual comprises measuring a standing height from the single image, and accounting for at least one of age, sex, race/ethnicity, weight, or height.

4. The method of claim 1, wherein estimating the body composition value comprises at least one of:
  estimating, by the processor, fat mass and fat-free mass,
  estimating, by the processor, a body density of the individual from an estimated body volume and a weight of the individual,
  estimating, by the processor, relative adiposity, percentage fat mass, and/or percentage fat using a relation that directly relates the percentage fat to the body density, or
  estimating, by the processor, body volume.

5. The method of claim 1, wherein determining the $VO_2$ max of the individual further comprises:
  measuring the distance the individual walks or runs, and the amount of time to cover the distance; and
  determining the $VO_2$ max using the measured heart rate, the distance and the amount of time.

6. The method of claim 5, wherein the mobile device is a smartphone, wherein the distance and the amount of time are measured using the smartphone.

7. A system of determining fitness of an individual, the system comprising:
  a mobile device including an image capture device comprising a camera sensor, wherein the mobile device is one of a smartphone or tablet; and
  a computing device in electronic communication with the mobile device configured to:
  obtain, via the camera sensor, a single two-dimensional (2D) image of the individual comprising an anterior or posterior portion of a body of the individual with hips and shoulders parallel to the camera sensor;
  digitize the single image of the individual into an array of pixels;
  identify, using a digital anthropometer on the mobile device, a plurality of anatomical landmarks in the digitized single image, including at a waist landmark, a hip landmark, and a shoulder landmark;
  measure, using an automated image analysis program that is configured to measure the array of pixels, a cross-sectional diameter as a linear distance of pixels in the single image at each of the plurality of anatomical landmarks;
  estimate, using a predictive model, a body composition value of the individual based on the measured cross-sectional diameters;
  determine a $VO_2$ max of the individual based on a measured heart rate of the individual while walking or running a distance over an amount of time;
  determine a fitness value of the individual using the determined body composition value and the determined $VO_2$ max, wherein the fitness value is indicative of the individual's aerobic fitness and/or cardiovascular health; and
  output the fitness value to a display of the mobile device via an application executing on the mobile device, wherein the fitness value is used to monitor changes to the individual's aerobic fitness and/or cardiovascular health over time.

8. The system of claim 7, wherein measuring each of the cross-sectional diameters comprises adjusting for standing height.

9. The system of claim 7, wherein estimating the body composition value of the individual comprises measuring a standing height from the single image, and accounting for at least one of age, sex, race/ethnicity, weight, or height.

10. The system of claim 7, wherein determining the $VO_2$ max of the individual comprises:
  measuring the distance the individual walks or runs, and the amount of time to cover the distance; and
  determining the $VO_2$ max using the measured heart rate, the distance, and the amount of time.

11. The system of claim 9, wherein estimating the body composition value comprises at least one of:
  estimating fat mass and fat-free mass,
  estimating a body density of the individual from an estimated body volume and a weight of the individual,
  estimating relative adiposity, percentage fat mass, and/or percentage fat using a relation that directly relates the percentage fat to the body density, or
  estimating body volume.

* * * * *